(12) United States Patent
Duggirala et al.

(10) Patent No.: US 7,244,230 B2
(45) Date of Patent: Jul. 17, 2007

(54) COMPUTER AIDED DIAGNOSTIC ASSISTANCE FOR MEDICAL IMAGING

(75) Inventors: Bhavani Duggirala, Bellevue, WA (US); Diane S. Paine, Redmond, WA (US); Dorin Comaniciu, Princeton Junction, NJ (US); Arun Krishnan, Exton, PA (US); Xiang Zhou, Plainsboro, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 225 days.

(21) Appl. No.: 10/702,721

(22) Filed: Nov. 6, 2003

(65) Prior Publication Data

US 2004/0147840 A1 Jul. 29, 2004

Related U.S. Application Data

(60) Provisional application No. 60/425,184, filed on Nov. 8, 2002.

(51) Int. Cl.
*A61B 5/00* (2006.01)
*A61B 8/00* (2006.01)

(52) U.S. Cl. .................. 600/300; 600/443; 128/925

(58) Field of Classification Search ........ 600/300–561, 600/586–595; 128/920–925; 706/14, 16, 706/18, 20, 25–27, 38, 41
See application file for complete search history.

(56) References Cited

U.S. PATENT DOCUMENTS

| | | | |
|---|---|---|---|
| 5,235,510 A | 8/1993 | Yamada et al. | |
| 5,553,620 A * | 9/1996 | Snider et al. | 600/440 |
| 5,596,993 A | 1/1997 | Oriol et al. | |
| 5,769,074 A | 6/1998 | Barnhill et al. | |
| 5,776,063 A | 7/1998 | Dittrich et al. | |
| 5,799,100 A | 8/1998 | Clarke et al. | |
| 5,839,438 A | 11/1998 | Graettinger et al. | |
| 5,878,746 A * | 3/1999 | Lemelson et al. | 600/407 |
| 5,999,639 A | 12/1999 | Rogers et al. | |
| 6,021,404 A * | 2/2000 | Moukheibir | 706/46 |
| 6,031,929 A * | 2/2000 | Maitz et al. | 382/132 |
| 6,032,678 A | 3/2000 | Rottem | |
| 6,063,030 A * | 5/2000 | Vara et al. | 600/437 |
| 6,090,044 A | 7/2000 | Bishop et al. | |
| 6,246,782 B1 | 6/2001 | Shapiro et al. | |
| 6,320,976 B1 | 11/2001 | Murthy et al. | |
| 6,574,304 B1 * | 6/2003 | Hsieh et al. | 378/62 |
| 6,748,044 B2 * | 6/2004 | Sabol et al. | 378/4 |
| 6,901,277 B2 * | 5/2005 | Kaufman et al. | 600/407 |

(Continued)

OTHER PUBLICATIONS

"Efficient Interpretation Policies", Isukapalli et al., in Proc. IJCAI, 2001.

(Continued)

*Primary Examiner*—Francis J. Jaworski

(57) ABSTRACT

Various attributes for medical CAD analysis used alone or in combination are disclosed, including: (1) using medical sensor data and context information associated with the configuration of the medical system to provide recommendations for further acts to be performed for more accurate or different diagnosis, (2) recommending further acts to be performed and providing an indication of the importance of the further act for further diagnosis, (3) distributing the computer-assisted diagnosis software and/or database over multiple systems, and (4) transmitting patient data to a remote system for CAD diagnosis and using the results of the CAD diagnosis at the remote facility.

21 Claims, 3 Drawing Sheets

U.S. PATENT DOCUMENTS

| | | | |
|---|---|---|---|
| 2002/0154822 A1* | 10/2002 | Nachtomy et al. | 382/232 |
| 2003/0120133 A1 | 6/2003 | Rao et al. | |
| 2003/0120134 A1 | 6/2003 | Rao et al. | |
| 2003/0120458 A1 | 6/2003 | Rao et al. | |
| 2003/0120514 A1 | 6/2003 | Rao et al. | |
| 2003/0125984 A1 | 7/2003 | Rao et al. | |
| 2003/0125985 A1 | 7/2003 | Rao et al. | |
| 2003/0125988 A1 | 7/2003 | Rao et al. | |
| 2003/0126101 A1 | 7/2003 | Rao et al. | |
| 2003/0130871 A1 | 7/2003 | Rao et al. | |
| 2003/0177038 A1 | 9/2003 | Rao | |
| 2004/0133083 A1 | 7/2004 | Comaniciu et al. | |
| 2004/0172297 A1 | 9/2004 | Rao et al. | |
| 2004/0193036 A1 | 9/2004 | Zhou et al. | |
| 2005/0049495 A1 | 3/2005 | Sumanaweera et al. | |

OTHER PUBLICATIONS

"Filters, Wrappers and a Boosting-Based Hybrid for Feature Selection", S. Das, in Proc. ICML, 2001.

"Vision for Mobile Robot Navigation: A Survey", DeSouza et al., IEEE Transactions on Pattern Analysis and Machine Intelligence, vol. 24, No. 2, Feb. 2002, pp. 237-267.

"Some Solutions to the Missing Feature Problem in Vision", Ahmed et al., Advances in Neural Information Processing Systems 5, Morgan Kaufmann Publishers, San Mateo, CA.

"Autonomous Exploration Using Multiple Sources of Information", Moorehead et al., Proceedings of the 2001 IEEE Int'l Conference on Robotics & Automation, Seoul, Korea, May 21-26, 2001, pp. 3098-3103.

"A Mathematical Programming Approach to the Kernel Fisher Algorithm", Mika et al., in NIPS 13, 2001.

"Using Mutual Information for Selecting Features in Supervised Neural Net Learning", R. Battiti, IEEE Transactions on Neural Networks, vol. 5, No. 4, Jul. 1994, pp. 537-550.

"Learning from Incomplete Data", Ghahramani et al., in NIPS6, 1994.

"Active Sensing for Robotics—A Survey", Mihaylova et al, in Proc. 5th Int'l Conf. on Numerical Methods and Applications, 2002.

"Learning Active Vision", Kappen et al., in Proc. ICANN, Oct. 1995.

"Active Vision for Complete Scene Reconstruction and Exploration", Marchand et al., IEEE Transactions on Pattern Analysis and Machine Intelligence, vol. 21, No. 1, Jan. 1999, pp. 65-72.

"Transinformation for Active Object Recognition", Schiele et al., ICCV, 1998.

"Information Theoretic Sensor Data Selection for Active Object Recognition and State Estimation", Denzler et al., IEEE Trans. On Pattern Analysis and Machine Intelligence, vol. 24, No. 2, Feb. 2002, pp. 145-267.

"Feature Space Trajectory Methods for Active Computer Vision", Sipe et al., IEEE Trans. On Pattern Analysis and Machine Intelligence, vol. 24, No. 12, Dec. 2002, pp. 1634-1643.

"Viewpoint Selection by Navigation through Entropy Maps", Arbel et al., ICCV, Corfu, Greece, Sep. 1999.

"Training Neural Networks with Deficient Data", Tresp et al., Advances in Neural Information Processing Systems 6, San Mateo, CA, Morgan Kaurman, 1994.

"Medical Image Databases: A Content-based Retrieval Approach", American Medical Informatics Association, http://www.pubmedcentral.nih.gov/articlerender.fcgi?artid=61234.

"Classification Driven Semantic Based Medical Image Indexing and Retrieval", Liu et al., 1998 Carnegie Mellon University.

"Fast and Effective Retrieval of Medical Tumor Shapes", Korn et al., IEEE Transactions on Knowledge and Data Engineering, vol. 10, No. 6, Nov./Dec. 1998, pp. 889-904.

"Joint Induction of Shape Features and Tree Classifiers", Geman et al., May 1996.

"Image-guided decision support system for pathology", Comaniciu et al., Machine Vision and Applications (1999), pp. 213-224.

"Content-Based Retrieval from Medical Imaging Databases: A Synergy of Human Interaction, Machine Learning and Computer Vision", Brodley et al., 1999, American Assoc. for Artificial Intelligence.

"Toward Validation Databases for Medical Imaging: Engineering a Scientific Rendezvous", Yoo, National Library of Medicine, National Institutes of Health, Bethesda, MD.

"Content-Based Image Retrieval in Medical Applications: A Novel Multi-Step Approach", Lehmann et al., Part of the IS&T/SPIE Conf. on Storage and Retrieval for Media Databases 2000, San Jose, CA, Jan. 2000, SPIE vol. 3972, pp. 312-320.

* cited by examiner

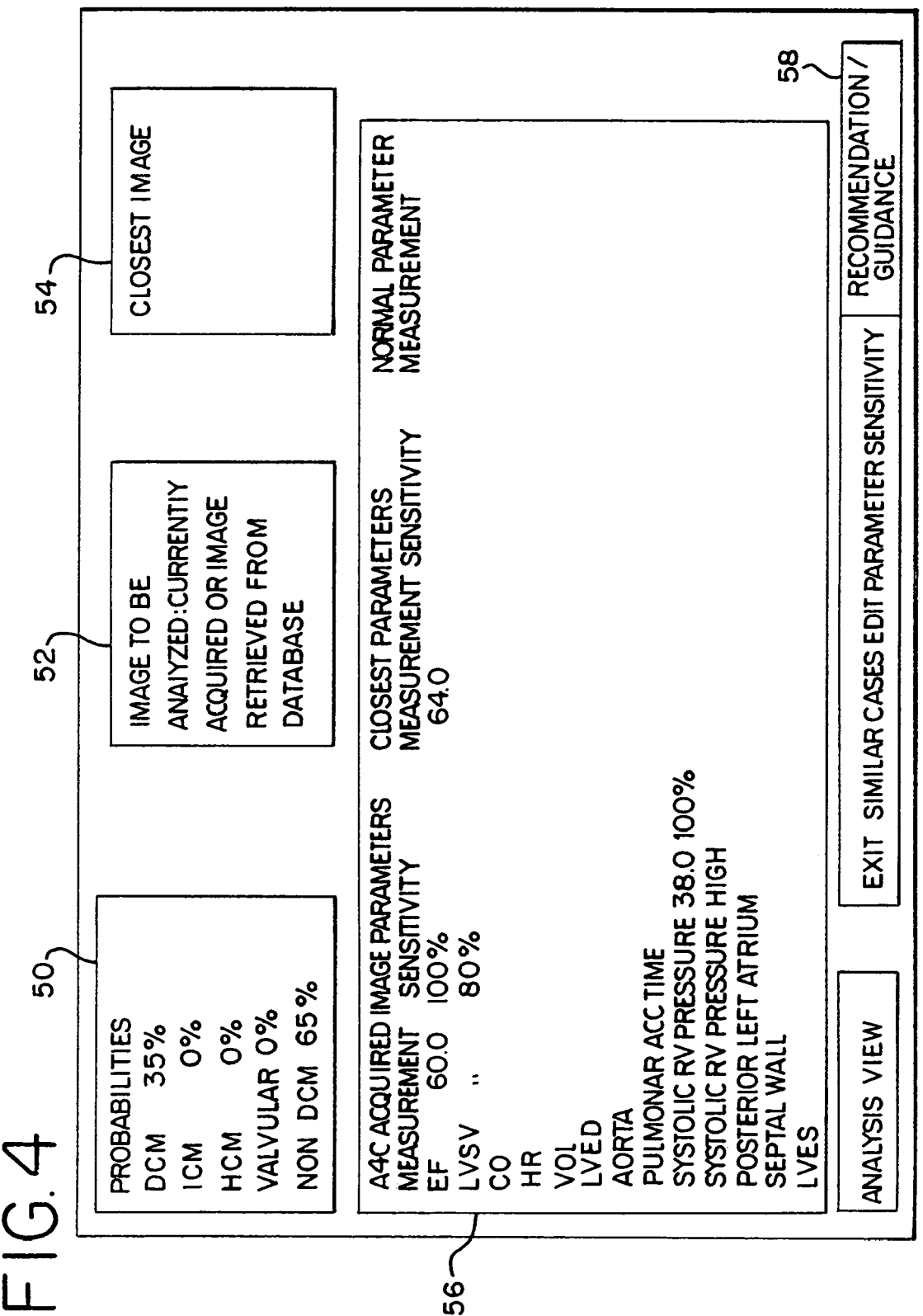

COMPUTER AIDED DIAGNOSTIC ASSISTANCE FOR MEDICAL IMAGING

REFERENCE TO RELATED APPLICATIONS

The present patent document claims the benefit of the filing date under 35 U.S.C. §119(e) of Provisional U.S. patent application Ser. No. 60/425,184, filed Nov. 8, 2002, which is hereby incorporated by reference.

This application is being filed on the same day as application Ser. No. 10/702,984 now U.S. Pat. No. 7,087,018 and pending application Ser. No. 10/703,024 which in turn derive from Provisional filings, 60/425,800 and 60/454,112 with respective filing dates of Mar. 12, 2003 and Nov. 13, 2002, the disclosures of which are incorporated herein by reference.

BACKGROUND

The present invention relates to computer-assisted diagnosis. In particular, architectures for computer-assisted diagnosis (CAD) systems and guidance for increasing the probability of a diagnosis are provided.

CAD subsystems are used for X-ray mammography. Using filters, neural networks or other CAD processes, regions of suspected lesions or microcalcifications are identified. The regions are then highlighted to the user for review and diagnosis. However, this feedback provides limited information to the user for assisting in diagnosis.

In medical diagnostic ultrasound imaging, limited diagnostic guidance is provided. Since ultrasound images may be easier to interpret better by experienced users, novice users may have trouble following protocols and interpreting images or identifying associated measurements needed or useful for diagnosis. Novice sonographers or even experienced sonographers using transducer probes with difficulty to position or interpret scan planes may spend more time or not attain as ideal information as possible. Ultrasound systems typically have on-line or system-based help functions. The user searches or otherwise identifies a subject of interest and the system provides a prepared text regarding the subjective interest. The help is organized in terms of contents, index or search topics directed to operation or use of the ultrasound system. However, limited or no information is provided for assisting in diagnosis.

BRIEF SUMMARY

By way of introduction, the preferred embodiments described below include methods and systems for assisting in medical diagnosis of a patient with a computer assisted diagnosis system. Various attributes used alone or in combination are disclosed, including: (1) using medical sensor data and context information associated with the configuration of the medical system to provide recommendations of further acts for more accurate or different diagnosis, (2) recommending further acts to be performed and providing an indication of the importance of the further act for diagnosis, (3) distributing the computer assisted diagnosis software and/or database over multiple systems, and (4) transmitting patient data and additional exam information (camera data, system configuration data, ultrasound data, ECG data . . . ) to a remote facility for CAD diagnosis or guidance and using the results of the CAD diagnosis and guidance at the remote facility. Additional or different attributes are provided in the discussions below.

Context information is used for CAD analysis. The system context, such as the type of system, configuration of the system for a particular exam, available system features, location of the system, or the type of sensor is used with data acquired by the medical system for CAD diagnosis. Patient context, such as the age, sex, race, body mass, previous diagnosis, symptoms, previous medical images, or other patient specific information is provided for CAD diagnosis. Based on either of the system or patient context, further acts for diagnosis are suggested to the user. For example, measurements, performing protocols, national and institutional guidelines, additional images, additional image views or obtaining history information are suggested to assist diagnosis. Comparative images, guidelines or assisted protocol specific to disease or information associated with the current context may be provided to the user for differential analysis.

For distributed architecture, a database in the medical system has a limited set of representative cases for comparison or other CAD processing. A larger database of a more comprehensive set of cases is provided on a different system or portion of the CAD database. If the user configures a medical system for context of imaging not available in the local database, the CAD processes then are performed by the remote processor or database information is requested from the remote processor for CAD processing locally at the medical system. If the medical system is configured for a non-networked environment, database information is requested through removable media such as CD or memory card.

To assist the user in diagnosis, the CAD subsystem provides quantitative and visual information. The CAD subsystem may be totally integrated into medical system, distributed or self contained system. The CAD subsystem outputs information, such as a rank or value, indicating the importance of an act in the CAD diagnostic determination. Based on the importance, a same act may be repeated or different acts may be performed to increase a probability of proper diagnosis. Measurements, images, imaging views, context information or other data may be recommended.

In a first aspect, a method for assisting a medical diagnosis of a patient with a computer assisted diagnosis system is provided. A medical system is configured for a particular examination. Medical sensor data is obtained in response to the configuration. Context data based on the configuration is also obtained. The medical sensor data and the context data are analyzed with a processor. A further act for diagnosis based on the analysis is automatically recommended.

In a second aspect, a method for assisting a medical diagnosis of a patient with a computer assisted diagnosis system is provided. Medical sensor data is obtained. The medical sensor data is analyzed with the computer assisted diagnosis system. A further act for diagnosis based on the analysis is recommended. A sensitivity of the diagnosis to the further act is indicated to the user.

In a third aspect, a method for assisting a medical diagnosis of a patient with a computer assisted diagnosis system is provided. Medical sensor data is obtained with a medical system. The medical sensor data is analyzed with the computer assisted diagnosis system. A further act to assist diagnosis based on the analysis is identified. The further act is automatically performed with the medical system. A diagnosis or guidance is output based on the further act and the medical sensor data.

In a fourth aspect, a system for computer assisted diagnosis in medical diagnostic ultrasound is provided. A medical diagnostic ultrasound imaging system has a memory. The memory is operable to store a first portion of a computer assisted diagnosis system. A processor associated with a second memory remote from the medical diagnostic ultrasound system is provided. This additional memory is operable to store a second portion of the computer assisted diagnosis system. The second portion is operable on data received from the first portion of the computer assisted diagnosis system.

In a fifth aspect, a method for computer assisted diagnosis in medical diagnostic ultrasound is provided. Ultrasound data is obtained with a portable ultrasound system. The ultrasound data is transmitted to a computer assisted diagnosis system at a facility remote from the portable ultrasound system. The ultrasound data is analyzed with a computer-assisted diagnosis system. Results of the analysis are output for use at the facility. The output results may also be provided back to the portable ultrasound system.

In sixth aspect, a system for computer assisted diagnosis in medical portable ultrasound is provided. A medical portable system is connected to a remote server through wired or wireless media, such as cellular or other mechanism. The system detects automatically network media type, available bandwidth and sends low quality images for guidance and high quality images for diagnostic assistance.

In seventh aspect, the portable ultrasound system data is transmitted to a remote computer assisted diagnosis system along with the anatomical position through a built in camera module. The ultrasound data and camera module data is analyzed for correct view, and remote guidance may also be provided to position the sensor at a correct anatomical position.

The present invention is defined by the following claims and nothing in this section should be taken as a limitation on those claims. Further aspects and advantages of the invention are discussed below in conjunction with the preferred embodiments.

BRIEF DESCRIPTION OF THE DRAWINGS

The figures are not necessarily to scale, emphasis instead being placed upon illustrating the principles of the invention. Moreover, in the figures, like reference numerals designate corresponding parts throughout the different views.

FIG. 4 is a representation of a display of one embodiment providing recommended further acts and associated sensitivities to the user.

DETAILED DESCRIPTION OF THE DRAWINGS AND PRESENTLY PREFERRED EMBODIMENTS

To assist both novice and experienced sonographers, an on-line knowledge base, such as a computer assisted diagnosis system, is provided for dynamic or static access to information. For static access to information, a menu structure is provided for selecting different pathology, symptoms or conditions. Various measurements, protocols, views or other information are recommended based on the selections. The selection is assisted by display of representative samples in addition to displaying current images. For dynamic assistance, a CAD subsystem provides a diagnosis and/or recommends further acts. The further acts are provided for increasing the diagnostic reliability of the CAD subsystem for a given examination. The importance of the further acts to the diagnosis may also be provided. These further acts, such as measurements and guidance, are provided either automatically, guided or manually.

For example during an echocardiograph exam, the number of possible measurements is in the hundreds. For a typical echocardiograph exam, many experienced sonographers perform about fifty different measurements. The CAD subsystem provides context sensitive real time guidance to determine additional acts, such as additional measurements, to be performed. By identifying a minimal number of measurements needed to be performed for reliable medical diagnosis, costs may be reduced. Data received from the medical sensor and context information are analyzed with a training module or other CAD based analysis, such as probabilistic classifiers or neural networks. Based on the analysis, recommendations for further acts, such as further measurements, are provided. The sensitivity of the diagnosis to the further act may also be indicated. For any given medical diagnosis, various features (e.g., measurements, images, or patient context) are uncertain but to different degrees with respect to a particular diagnosis. For example, a measured feature may contain lower uncertainty while a missing feature may have maximal uncertainty. The contextual information and medical scan data is analyzed to determine the relative sensitivity of the features or acts on the CAD training sets. The analysis determines whether more measurements should be taken, such as unmeasured features or accuracy of previously measured features. The additional measurements or other acts to address or decrease the uncertainty are recommended to the user or automatically performed by the medical system to increase the diagnostic probabilities of the CAD subsystem.

Figure 1:
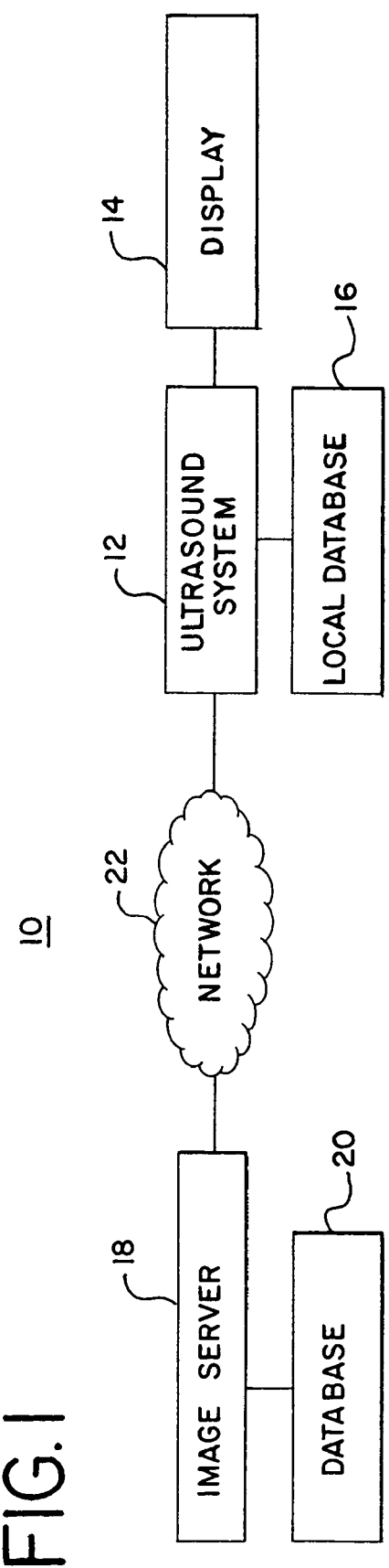
FIG. 1 is a block diagram of one embodiment of a computer assisted diagnosis system used with a medical system.
Figure 2:
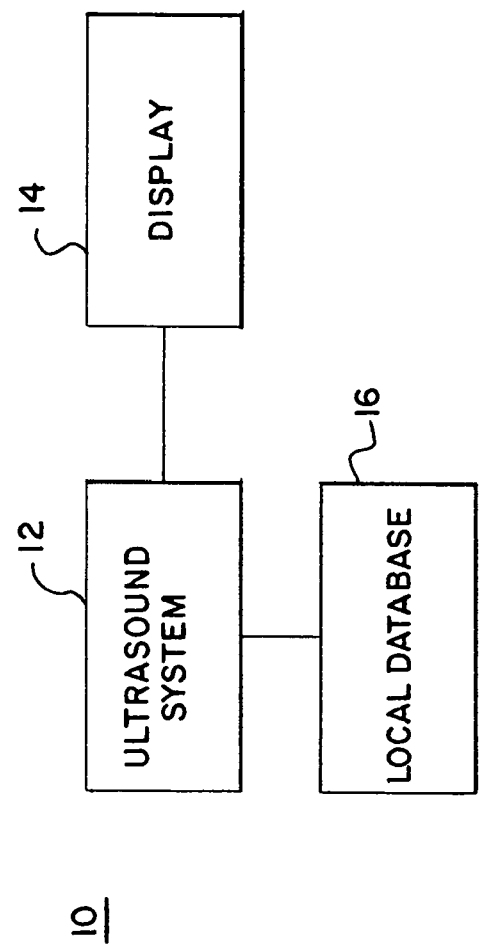
FIG. 2 is a block diagram of an alternative embodiment of the computer assisted diagnosis system.

The CAD subsystem is either distributed over two or more systems, such as shown in FIG. 1, or is resident on a medical sensor or one system (e.g., on a remote web and database server), such as shown in FIG. 2. FIG. 1 shows one embodiment of a system for computer assisted diagnosis in medical diagnostic ultrasound with a distributed CAD subsystem. While shown for medical diagnostic ultrasound, other medical sensors may be used, such as X-ray, CAT, MRI, or other now known or later developed medical sensors for imaging. The system 10 includes the medical system 12, the display 14, a local memory 16, an image server 18, a memory 20 and a network 22. Additional, different, or fewer components may be provided.

The medical system 12 is any now known or later developed device for obtaining information representing a patient, such as an X-ray, MRM, or ultrasound scanning device. In one embodiment, the medical system 12 is a medical diagnostic ultrasound imaging system. For example, a portable (e.g., handheld) medical diagnostic ultrasound imaging system is provided, but cart based systems may be used. A portable ultrasound system may include only an ultrasound scanner and associated display and communications hardware, but may alternatively include other devices, such as a digital camera, a glucose test system, an electronic stethoscope, a pulsimeter, ECG, NIBP, IBP, RESP and/or other device. As another example, the ultrasound system is in an emergency vehicle, such as an ambulance. Other medical sensors (e.g., X-ray or MRI) and associated systems may be used. In one embodiment, the medical system 12 is one of a plurality of separate medical systems of a same or different type at a particular site. A plurality of sites may then communicate with the processor 18.

The display 14 and local memory 16 are part of the medical system 12, such as being a CRT, flat screen, LCD or other display 14 of the medical system 12 and a removable storage device, RAM, ROM or other memory of the medical system 12, respectively. The local database 16 of the medical system 12 is operable to store a first portion of a computer-assisted diagnosis system. For example, the software and/or database for implementing a CAD subsystem is provided in the local database 16. The portion of the database for the CAD subsystem may include one or more sets of data for a particular condition, representative image sets, representative measure sets, training models or other information used to implement a computer-assisted diagnosis system. In one embodiment, the computer-assisted diagnosis system is operable to perform a diagnosis based on information within the first database without reference to the distributed other portion in the memory 20. For example, the local memory 16 includes a representative sample of the other memory 20. A sample of all various sets of data is provided in one embodiment, or a sample of one set of data out of many is provided in another embodiment. For example, database information for a first type of pathology is provided at the local memory 16 and data for a plurality of different pathologies is provided at the other memory 20. As another possible division, the local memory 16 is operable to implement a first set of diagnostic capabilities. The other memory 20 is operable to provide additional or different diagnostic capabilities. For example, diagnosis for different conditions, the number of feature vectors used to identify a particular diagnosis, the output information, the type of pathology, the type of inputs considered, or other now known or later developed capabilities of a computer assisted diagnosis system are provided at different levels from the local memory 16 than from the other, remote memory 20.

In one embodiment, the medical system 12 is operable to acquire an image, such as an ultrasound image. The image is acquired by scanning, such as with ultrasound, X-ray or electric field energy. Alternatively, an image is retrieved from the memory 16 of the medical system 12 or the other memory 20 remote from the medical system 12. A single image or a sequence of images from same or different modalities may be obtained. The image, context information, measurements and/or other information is then used for CAD analysis with CAD information in the local memory 16.

In one embodiment, the local memory 16 includes a menu structure of possible pathologies, associated conditions and associated representative samples. The remote memory 20 includes additional possible pathologies, associated conditions and associated representative samples. The menu structure allows for static selection of different pathologies, conditions or symptoms during use. The user is then guided to perform particular measurements or other acts for diagnosis.

In one embodiment, the local memory 16 includes a catalog of diseases and associated anatomy, such as a catalog sorted by anatomy with subheadings sorted by different diseases. Different arrangements of information may be provided. Based on a current examination or study and selected disease or anatomy information, the CAD subsystem determines an associated disease using the local CAD database in the memory 16. The training model or associated predicate information is stored on the local memory 16 or the remote memory 20. If no disease match is found based on the local database information, the medical system 12 is operable to request information or analysis from the remote database. For example, a subset of the database is loaded onto the medical system 12. The new database information is cached by the medical system 12 on the local memory 16 for CAD analysis. The information downloaded from the remote database is identified based on the system context and the local database size. Where minimal memory is available, such as in a small portable device, the context information and the data obtained by the medical sensor, such as an image, are transmitted over the network 22 to the remote portion of the CAD subsystem. The results of any further CAD processing are then transmitted back from the processor 18 to the medical system 12 or output at a medical facility.

Information may be transmitted between the medical system 12 and the processor 18 over the network 22. The network 22 comprises a single direct link, an intranet, the Internet, a telephone connection, a modem connection, an Ethernet connection or any other now known or later developed connection for allowing communications between two devices. In one embodiment, the network 22 comprises wireless transmitters and receivers for wirelessly communicating between the medical system 12 and the processor 18. Data transmitted over the network 22 is in any of various formats, such as a DICOM protocol, an XML spreadsheet, or other now known or later developed formats or protocols.

The processor 18 is an image server, server, microprocessor, personal computer, medical system, networked patient data recovery system, or other now known or later developed device for processing image, patient context, system context, measurements or other information for computer-assisted diagnosis. The processor 18 is associated with the memory 20. The memory 20 is a RAM, ROM, tape, hard drive, removable storage, permanent storage, or other now known or later developed memory device.

The processor 18 and associated memory 20 are remote from the medical system 12 in one embodiment. For example, the processor 18 is in a different medical facility than the medical system 12. As another example, the medical system 12 is in a vehicle or a portable system for use external to a facility, and the processor 18 is located at a medical facility or located remotely for use at the medical facility. In yet another embodiment, the processor 18 is associated with remote expert processing as disclosed in (application Ser. No. 10/654,509, filed on Sep. 3, 2003), the disclosure of which is incorporated herein by reference.

The memory 20 is operable to store a portion of a computer assisted diagnosis system. For example, a database representing all or a subset of information used by a CAD subsystem is stored in the memory 20. The database information corresponds to information stored in the memory 16. In one embodiment, the database information in the memory 20 is a more comprehensive or has more information than the information stored in the memory 16 associated with the medical system 12. In alternative embodiments, the memory 16 is more comprehensive for all or a subset of information than the memory 20. In another embodiment, different software processes, algorithms or underlying data for implementing diagnosis of different pathologies, performance of different diagnostic capabilities, relational comparison for diagnosis or determining a probability of diagnosis are provided with the memory 20 than are provided with the memory 16. For example, the memory 20 includes a hospital information system, a radiology information system, a clinical information system, a patient archival and storage system, a laboratory report system or other medical database information in one or distributed over a plurality of databases accessible by the processor 18. Any organization of the information may be used, such as reference images in one group, feature vectors or other symbolic information in another group, disease information in another group, and indications in yet another group organized by organ or anatomy. In one embodiment, synchronization is provided between the memories 16, 20 so that the overall CAD subsystem 10 operates in an expected distributed manner.

Requests, data, algorithms or other CAD information provided from the memory 16 of the medical system 12 to the processor 18 and associated memory 20 is usable by the processor 18 and associated memory 20 or corresponding portion of the CAD subsystem. For example, the portion of the CAD subsystem implemented by the processor 18 and memory 20 is operable to determine a diagnosis, determine a probability of diagnosis, recommend further acts, indicate a sensitivity of diagnosis to further acts or implement other CAD capabilities based on data provided from the medical system 12 or other portion of the CAD subsystem. In one embodiment, the portion of the CAD subsystem on the processor 18 and memory 20 is operable to provide data responsive to a diagnosis implemented in part or completely by the portion of the CAD subsystem implemented on the medical system 12 and associated memory 16. For example, the medical system 12 uses a processor to determine a high or medium probability diagnosis based on the training models or relational database stored on the memory 16. A higher probability diagnosis or confirmation of diagnosis is then performed using the processor 18 and associated memory 20. For example, additional context information, additional image information, additional measurements or other feature vectors used for CAD are used to confirm the diagnosis with the processor 18. In one embodiment, the processor 18 uses additional CAD feature vectors as compared to the medical system 12. As a result, a more accurate or higher probability diagnosis may be provided. As an alternative to CAD with different information or additional information, the portion of the CAD subsystem implemented by the processor 18 and associated memory 20 uses additional training models. The processor 18 then outputs the additional diagnosis information, further recommended acts, sensitivity of the further acts for diagnosis or other information to the medical system 12 or to any other communications device.

In one embodiment, the memory 20 includes additional patient context information, such previous diagnosis, previous images, previous measurements, or other information and is operable to perform further CAD diagnosis based on the additional information or provide the additional information to the medical system 12. In one embodiment, the actual CAD diagnosis is implemented in only one of the processor 18 or the medical system 12. Alternatively, both the processor 18 and medical system 12 implement the same or different CAD diagnosis based on the same or different information. Either the processor 18 or medical system 12 may provide information used by the other of the devices 18, 12 for CAD.

In one embodiment, the portable medical system 12 is connected to the remote server 18 through wired or wireless media, such as cellular. Any of now know or later developed format or type of connection may be used, including LAN, Wi-LAN (e.g., 802.11a or 802.11b), WAN (e.g., cellular—2G, 3G or 4G or satellite), USB, Firewire, cradle, Bluetooth, WPAN or others. The portable medical system detects automatically the network media type and associated available bandwidth. For example, the available bandwidth is programmed, set based on a selected connection route, determined by transmitting information and receiving a response (e.g., a ping), determined based on usage by others, determined based on transmitted bandwidth information or other now known or later developed techniques. The ultrasound data and/or other data for transmission are then altered as a function of the available bandwidth. For example, an amount of compression is used to match the available bandwidth (e.g., uncompressed, MPEG-2 at 1, 1.5, 2, 3, 5 or 15 Mbps, M-JPEG with a Q of 5, 15 or 20 or other compression algorithms or rates). Image size may also be considered for determining an amount of compression. The data bandwidth may also be matched to the available bandwidth as a function of a type of assistance. Lower quality (i.e., less data or more compression) is used for transmitting information to receive guidance without CAD analysis (e.g., menu based static assistance), and higher quality images are used for diagnostic assistance or CAD.

In another embodiment, a camera module is built into the portable ultrasound system 12, such as a CCD or other digital camera technology now known or later developed. The system 12 acquires scan data, such as from an ultrasound scan, as well as anatomical position data. The camera is used to acquire the anatomical position data, such as the position of the ultrasound probe relative to the patient. Other sources or anatomical position data may be used, such as orientation and position sensors on the probe. The scan data and the anatomical position data are transmitted for remote computer assisted diagnosis. The ultrasound data and camera module data is analyzed to determine whether a correct view or scan was acquired. For example, the probe position relative to the patient and/or the scan data indicate is analyzed to determine that a less than desirable or partial view of the anatomy of interest was acquired. A recommendation or further guidance is transmitted to the user of the portable ultrasound system to acquire a more complete or different scan for the correct anatomical position. A representation of the probe position or anatomy of interest may also be transmitted.

FIG. 2 shows an alternative embodiment of the system of FIG. 1. In this alternative embodiment, the CAD subsystem is resident on the medical system 12 and the associated memory 14. The CAD subsystem is at a single location or on a single device, such as the medical system 12. In this embodiment, the CAD subsystem implemented by the medical system 12 is undistributed. A network connection for requesting information or gathering other data for analysis by the CAD subsystem may be provided. Several of the methods described below may be implemented on either of a distributed or undistributed CAD subsystem.

Figure 3:
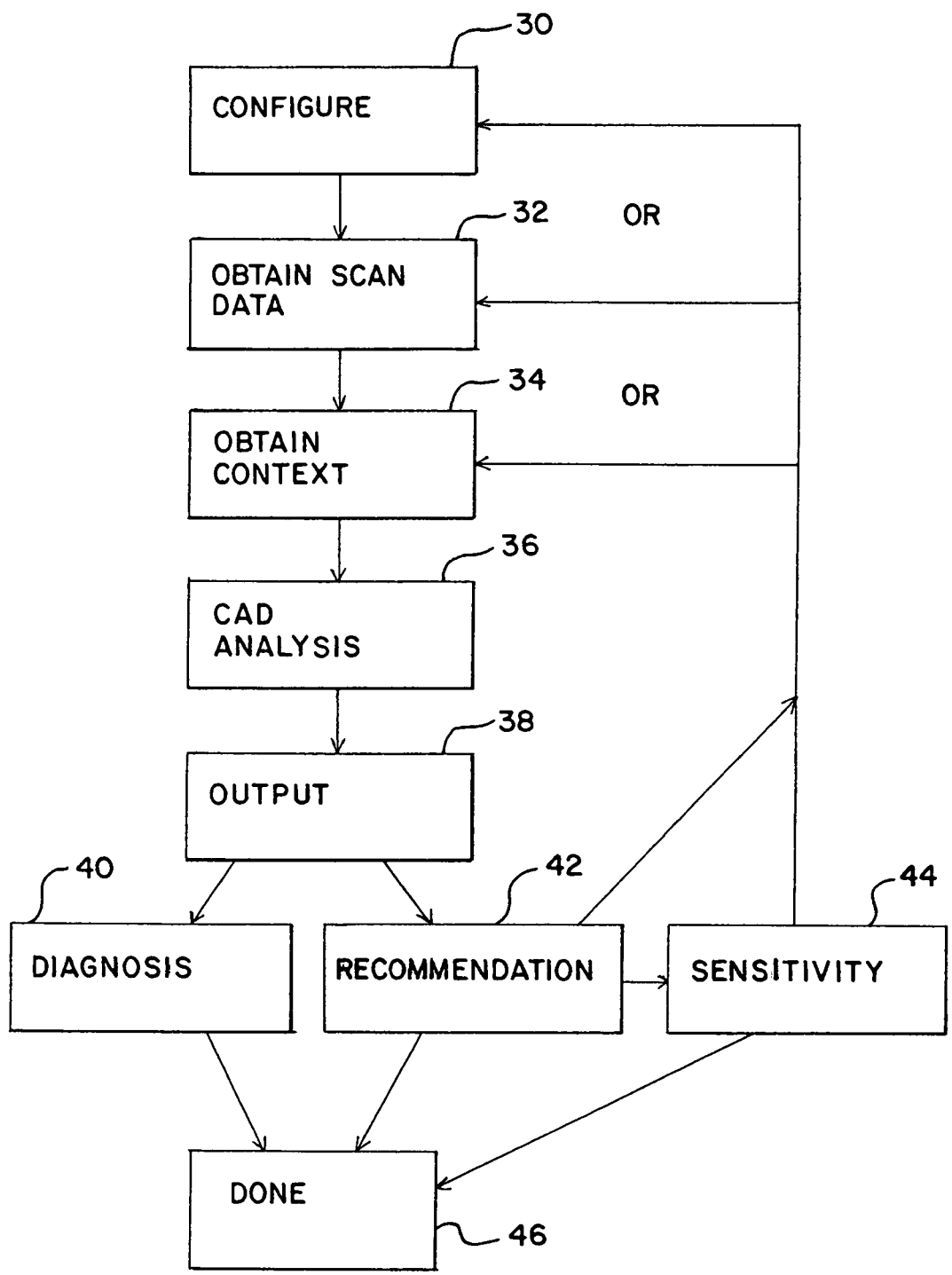
FIG. 3 is a flow chart diagram of one embodiment of a method for computer assisted diagnosis using a medical system.

FIG. 3 shows a flow chart of one embodiment of a method incorporating various attributes. Methods using fewer, different or additional acts than shown in FIG. 3 may be provided. For example, the act 34 is not provided, the act 44 is not provided, the feedback of acts 42 or 44 to acts 30, 32 and/or 34 is not provided, or the recommendation act 42 is not provided. Other examples include additional acts, such as using static navigation of a menu structure prior to CAD analysis with or without separately obtaining context information. The menu structure may also be used without the CAD analysis of act 36, such as providing user guidance through selection of anatomy, symptoms, conditions or diseases to identify additional or different measurements or other further acts without processor based analysis.

The flow chart of FIG. 3 represents one embodiment of a CAD subsystem for use with medical diagnostic ultrasound or other medical sensors to assist in medical diagnosis of a patient. In general, image information and other context information are obtained. The input information is segmented into feature vectors and used to trigger one or more classifiers (e.g., training models) for performing CAD analysis. One or more algorithms perform the segmentation and identification of feature vectors based on the system context, such as configuration for examining a particular anatomy. Using a database of feature vectors and images in comparison to the current image and the associated segmented feature vectors, a classifier or training model determines a probability of a particular. diagnosis or a multiple different diagnosis. Visual aids for diagnosis are output, such as one or more of recommended further acts, a sensitivity matrix of the further acts for diagnosis, a probability of accuracy of the diagnosis, interactive guidance, a checklist, national guidelines, institutional guidelines or other information associated with a diagnosis. Due to the recommendations of further acts to improve diagnosis, work flow and effectiveness may be improved while reducing subjectivity and variability.

In act 30, a medical system is configured for a particular examination. For example, a medical diagnostic ultrasound system is configured to perform a scan of the heart or a particular region of the heart for an echocardiograph study. As another example, a medical diagnostic ultrasound system is configured to scan a breast of a patient. As yet another example, a medical diagnostic ultrasound system is configured to scan a uterus or a fetus. Any of various now known or later developed configurations may be provided. For example, many medical diagnostic ultrasound systems from different manufacturers provide a same set or different sets of settings adapted to scan a particular anatomy, for a particular diagnostic process, for a particular protocol, or for a particular disease. Transmit beamformer, receive beamformer, the type of transducer, filtering, image processing, the type of detection, the type of image processing or other medical imaging parameters are set based on the configuration. Setting any of these parameters or devices also acts to configure the medical system. Other configuration settings or triggers include selecting a scan location or viewing angle.

In one embodiment, the user configures the medical system by selecting a particular application or examination from a menu, a list or using a graphic user interface. In other embodiments, the medical system is configured by selecting specific ones of various imaging or scanning parameters for the medical system. In yet other embodiments, the medical system is configured by trigger, such as selection of a particular transducer and connection of the transducer to the medical system. Any now known or later developed techniques or combination of techniques may be used for configuring the medical system. The medical system is configured to obtain data. For example, a particular transducer is selected and connected to an ultrasound system. The transducer is associated with scans of a particular type or types of examinations and not of other types of examinations or another particular examination. Where a patient is seeking diagnosis or a particular type of examination, the medical system is configured for scanning the associated anatomy in one or more modes, such as B-mode, C-mode, Doppler, M-mode, spectral Doppler, Doppler tissue imaging, strain imaging, elasticity imaging, shear wave imaging, acoustic streaming, acoustic palpation, harmonic imaging, boost imaging, 3-D, 4-D, X-ray, MRI or other now known or later developed modalities. Doppler tissue imaging is using a Doppler technique for estimating tissue motion. Strain imaging and elasticity imaging are techniques to estimate the elastic modulus of tissue. Shear wave imaging is a technique to estimate the shear modulus of tissue. Acoustic streaming is a technique for using acoustic force to create flow and measuring that flow. Acoustic palpation is a technique for using acoustic force to move tissue and then measure the tissue relaxation characteristics. Harmonic imaging is a technique for imaging outside of the fundamental transmit frequency band. Boost imaging is a technique for increasing the acoustic transmission for a very short time for improved snapshot imaging. 3-D imaging is volume imaging, and 4-D imaging is volume imaging over time.

In some embodiments, diagnosis of the functionality of a particular anatomical structure depends on information from multiple modes. For example, to access myocardium viability and function, information about perfusion, motion and thickness is obtained. The medical system 12 may be configured to operate in one mode or a plurality of modes sequentially to obtain the information. Combination of modalities may assist in understanding and evaluating different ischemic processes. Fusion of information from multiple sources may increase confidence or sensitivity. As a result, different images, studies or types of information are available for interpretation.

In act 32, medical sensor data is obtained. In response to the configuration of the medical system, the medical sensor scans a patient. The obtained medical sensor data is an image or sequence of images in one embodiment. For example, an ultrasound image, a B-mode image, an M-mode image, a Doppler image, a three-dimensional image, a harmonic image, a contrast agent image, an X-ray image, an MRI image or other now known or later developed medical system image is obtained. Other medical sensor data is obtained from the acquired image or directly by measurement of information not used to image. For example, a position of a spectral Doppler gate or M-mode line within a two-dimensional region is obtained. A position of a region of interest or other pointers for 2D, M-mode or Doppler imaging is identified. As yet another example, one or more measurements based, in part, on user input or automatic determination from the image information is obtained. For example in cardiology to assess cardiomyopathy, the left ventricular dimensions and volumes, wall thickness, ventricular mass, ventricular shape, global systolic function, regional systolic function, septal motion, presence of myocardium infarction or other now known or later developed measurements are made. Measurements based on information from other than the medical sensor scan are provided as part of the context discussed below. Other measurements, images or other medical sensor data are obtained from different configurations, for different diseases or different pathology. The images, image information, measurements or other obtained medical sensor data are used to form feature vectors either extracted automatically by segmentation algorithms or manually input by the user for use by the CAD analysis of act 36.

In one embodiment to assist in determining the measurements, configuring the system or other actions to be taken for obtaining the desired medical sensor data, a menu structure of possible pathology, associated conditions and associated representative examples is provided. For example, emergency response personnel have some sonography training but may lack comprehensive sonography experience. By navigating through a menu structure, the emergency response personnel are more likely to obtain information useful for diagnosis associated with a particular examination. The scanning is performed based on the navigation through the menu structure. The resulting medical sensor data, such as ultrasound data, more likely provides the desired medical sensor data. As a result, a mobile emergency response with a portable ultrasound system may be made more effective. A sonographer's use of a stationary or cart based ultrasound system in a medical facility may also be assisted.

The static system for assisting the user through menu navigation uses one or more of image comparison, annotation, measurement characteristics, or other parameters. Pathology, diseases, symptoms or other information is provided as a list for user selection. The user can search an image database for related anatomy or pathology and is provided with subclasses associated with the anatomy or pathology. For example, the aorta is selected and subclasses of coronary arteries, RCA-PDA or LMC-LAD, LCX are provided. Associated diseases may also be listed, such as aortic valve disease. Subclasses of diseases may be provided, such as aortic stenosis, sub-aortic stenosis, valvular aortic stenosis, or supra-valvular aortic stenosis. Word searching or hierarchal menu structures may be used. Alternatively, a list of all conditions associated with a class, subclass or the entire system is provided.

Based on the user choice, images associated with selected classes, subclasses, diseases, graphical representations of the probe position for scanning a desired anatomy, tips, protocols, related information, symptoms, modes of imaging, desired views or measurements are provided. In one embodiment, abnormal and normal representative images are provided. For example, left ventricular adult cardiac images representing dilated and hypertrophic cardiomyopathy images are provided. An associated degree of dilation or other characteristics of the images, selected class, subclass, measurements, symptoms or other characteristic are also provided. Suggested views for scanning may also be indicated, such as an apical four chamber view, a parasternal long axis view, a parastemal short axis chordal level view, or a parastemal short axis papillary muscle level view. The user compares images from the database to images of the current examination, such as providing a side-by-side view. By navigating through the menu structure and providing associated representative images, the sonographer may discriminate between suspected pathology in a current examination and pathology associated with a particular diagnosis or disease.

The menu structure may provide a normal range of measurements or other indication of calculations suggested for a selected disease, class, subclass, symptoms or pathology. The user may then compare measurements based on a current scan with the normal range of measurements associated with selected information. Additional information may be provided, such as a list of potential technical pitfalls associated with the selected information to further guide interpretation and diagnosis. A list of associated or differential diagnosis of particular pathological classes or subclasses may be provided. A list of required measurements, protocols or other further acts may be provided in one embodiment based on the selection by a user of a particular disease, pathology or other information. Suggested but not necessarily required measurements, views, protocols or other further associated with the selected information may also be provided. The provided information may be determined from any of various sources, such as the training information discussed below for CAD analysis.

In yet a further embodiment, a graphical representation of selected anatomy is provided. The graphical representation may show a location of a selected disease associated with anatomy, a view of the disease, distance information, or size information associated with the disease. The information provided may vary as a function of additional information, such as patient context information from a CAD analysis. Standard medical information, such as evaluation guidelines, may additionally be provided.

As an alternative to navigating through the menu structure, a sonographer uses their own experience or the experience of others to collect the desired information by configuring the ultrasound system or medical sensor. As yet another alternative, a sonographer collects material they believe is appropriate without reference to a particular knowledge base.

In act 34, context data is obtained. One or both of patient context and system context data may be obtained. System context data is based on the configuration of the medical system. For example, a profile associated with a current examination and a current user is provided. The profile information indicates the type of examination, type of imaging, the selected imaging application, the parameters used for configuring the medical system or other information relating to the configuration. In one embodiment, the user or sonographer is associated with a particular configuration or configurations, so that indication of a particular sonographer provides system context information. In one embodiment, the system context is provided by an indication of anatomy, pathology, pathology progression, patient identification, application or other information. The context is based on the current particular examination. For example, the system context is provided by detecting events associated with configuration, such as connection of a particular type of transducer, selection of an examination, selection of a measurement, selection of a plurality of different measurements in a particular grouping, navigation through and selection of menu information, or any other indication of the configuration of the medical system for a particular examination. In one embodiment, the system context data based on the configuration identifies a particular examination without reference to data obtained as a result of the configuration or obtained in response to the scan of act 32. Alternatively, image data, measurement data or other information obtained from the scan of the patient is used to identify the particular examination and provide the system context data.

Patient context data is obtained by user entry or by query to a database or other source of information. Patient context data originates from any number of sources of information including, but not limited to, vital statistics, patient symptoms and available test data. Vital statistics can include such information as a patient's ID number, height, weight, body mass index, date of birth, age, blood pressure measurement, temperature or any other personal medical data. Patients' symptoms may include for example, indications of pain, such as chest pain, shortness of breath, syncope, detection of a foreign mass in an area of tissue, cough, hemoptysis, labored breathing, poor circulation, unexpected weight loss or gain or any other system that may be material to a particular medical examination. Available testing data can come from a baseline scan, preliminary blood work or any other test that would be material to a particular medical examination. For example, a patient record of other clinical findings related to a current study or current system context is retrieved. As another example, a user is queried to input patient specific information, such as identification number, symptoms, sex, age, height, weight, race or other medical information for use in diagnosis or recordkeeping. In one embodiment, information from previous examinations or from different types of medical systems is obtained. For example, embedded image files or other measurements from a different system modality are acquired. Information from previous examinations of the same modality, such as a prior ultrasound examination findings or images, may be acquired. DICOM or other standard or non-standard formats may be used to get previous clinical history information. Alternatively, the information is scanned, accessed or otherwise input to the CAD subsystem or medical system.

The context data is provided to or from the medical system. For example, the medical system includes the context information within the memory as well as the information obtained by scanning with the medical system. The context data is used in conjunction with the sensor data to determine what, if any, further measurements may be taken by the system in order to provide computer assisted medical diagnosis. To make the determination, the context data and medical sensor data is provided in any of various formats to the CAD subsystem. For example, the CAD subsystem accesses the information as needed without any reformatting. As another example, the context data and/or sensor data are configured into a particular format for use by the CAD subsystem. In one embodiment, a database of current examination information is organized, such as using an object oriented database interface, a relational database interface or a simple file structure. For example, a DICOM specified format, text, an XML or other user defined format is provided. In an XML format, a header and data block is used to indicate any of the version number, file name, number of information object pointers, feature vectors or other segmented information, image data, measurement data, context data, organ name, measurements. Patient context and clinical information, such as patient demographics, history, physical exam findings, identification, age, sex, race, disease code, present disease code, past disease code or other sensor data. . Less or more information may be used.

In one embodiment, the CAD analysis is initiated in response to the user depressing a button or otherwise selecting CAD analysis. When the user depresses a button, an algorithm formats or otherwise obtains the information for use by the CAD subsystem. Alternatively, other user input is acquired before further acts are recommended and a possible diagnosis is provided. Further user guidance may be provided to assist in the CAD analysis. The user may be instructed to provide additional information either through further medical sensor examination, input by the user or a query to other sources of information.

In one embodiment, ultrasound data or other medical sensor data and context information are transmitted to a remote CAD subsystem or portion of a CAD subsystem. For example, ultrasound data and any available context data are transmitted from a portable ultrasound system to a remote facility, such as a medical facility. Additional context data may be acquired at the medical facility and used for CAD diagnosis or transmitted back to the portable ultrasound system for local CAD diagnosis in a distributed network, such as discussed above for FIG. 1.

In act 36, a CAD analysis is performed. Medical sensor data, such as ultrasound image data or associated measurements, is analyzed with a computer assisted diagnosis system. In one embodiment, context data, such as system context, patient context or combinations thereof is analyzed with the medical sensor data. For example, the patient context data or system context data is used to identify one or more diseases associated with a particular examination or symptoms for relative CAD analysis. A particular examination may be associated with one or more possible diseases. Using segmentation and a database, computer assisted diagnosis is performed.

The acquired information is segmented. In one embodiment, segmentation is performed automatically. For example, a processor identifies features of an image associated with a particular disease. Guided segmentation is provided in an additional or alternative embodiment, such as guiding the user to input additional information based on obtained data, such as tracing a region of interest or possible diseased area. Feature vectors for use in CAD analysis are extracted using image processing operations or manual guidance. Image comparison, texture determination, image features, image measurements or other image based feature vectors are identified. Segmentation algorithms may be configured in a pipeline order as individual components where one algorithm supplements another algorithm. Alternatively, segmentation is performed in parallel. Any of various algorithms, filters, quantifications, numerical characterizations, statistical information, comparative or representative texture or shape information, neural network, or other processing extracts feature vectors from any of the image information, system context or patient context information. The feature vectors to be extracted are identified by the possible disease states, based on other feature vectors, based on patient or system context or based on CAD analysis.

Once sufficient feature vectors are acquired, CAD analysis is performed. The number of feature vectors for proceeding with the CAD analysis is based on experimentation, iterative CAD analysis to provide a desired probability of diagnosis, user selected number of feature vectors, feature vectors identified pursuant to a specific medical protocol or other listing of feature vectors. The CAD analysis uses a database or databases with algorithms, feature vectors, images and/or other information.

For analysis, each of the possible diseases is modeled. Models are based on signs, symptoms, measurements, images or other information identified as important for discriminating between healthy and pathological conditions. One or more databases associated with one or more respective disease or disease categories are provided for the CAD analysis. The database represents a model of disease in pathology that maps experts' quantitative diagnostic methods for determining normal and abnormal disease measurements. The experts' qualitative methods may also be mapped. A model is a mathematical representation of the disease and symptoms based on the quantitative and qualitative information. For example, the database is populated with a hierarchy of logically and structurally related images, measurements, protocols or other information that provide a basic knowledge foundation. Association, relationship or aggregation of objects is used to populate the database. Using statistical information or other CAD subsystem processes, an amount of information and repetition of the information is provided in the database for sufficient diagnostic probability. In one embodiment, minimal operational information is one representative example of a measurement, image or other information of each disease for each organ. Each representative sample may be associated with a particular patient, other tracking information, time, image resolution, date of acquisition, name of file, image, three dimensional information, surface reconstruction, symbolic information, or other spatial information providing context for an image. Structural data providing information about a single object or knowledge providing information about a class of objects is associated with each of the samples. Feature vectors associated with each of the samples are provided to identify a range of normal versus abnormal associated with a disease.

In one embodiment, the CAD subsystem and associated database described in application Ser. Nos. 60/425,800 and 60/454,112, filed on the same day as the instant application, the disclosures of which are incorporated herein by reference, is used. Training models are stored in a database and used to perform feature sensitivity analysis. The training models contain a collection of data measurements relating to one or more particular medical conditions. For example, the database may contain a plurality of distributed data points relating to the likelihood of a patient having dilated cardiomyotomy (DCM) or a normal heart condition (non DCM). Such data may include measurements pertaining to the size of the heart, the thickness of the heart walls and the level of blood flow to and from the bean. One or more training models may be provided for each of the featured vectors or for each disease.

The training models are provided in reference to various information or feature vectors. For example, a relationship between a left ventricle dimension and a patient's height provides a distribution for one training model. The training model distribution indicates those combinations of measurements (e.g., feature vectors) that signify a high probability of DCM or non-DCM. Alternatively, a different training model distribution may indicate measurements that signify a high probability of non DCM. Other examples for different diseases or different training model distributions, using the same or different feature vectors, may be provided. For example, a patient with a height of 1.5 to 1.7 meters and a left ventricle dimension of 50-56 millimeters indicates a somewhat high probability of having a DCM. However, the same left ventricle dimension on a patient taller than 2 meters may indicate a probability of non DCM. The same measurement for a 1.1 meter child may indicate a very high probability of a DCM. An image having a distribution of signals more similar to a representative disease sample image than a representative healthy sample image indicates a probability of disease.

As another example, coronary artery disease is modeled for CAD analysis. The feature vectors used include systolic and diastolic function, stress echo information, myocardial perfusion (contrast echo examination information), infarction, wall thickness and fibrosis. Additional, different or fewer feature vectors may be used.

In addition to probability distributions for training models, other images, associated information or grouping of data may be provided. Any of possible database information is used with any of now known or later developed CAD subsystems may be provided. Using the CAD database or training models, CAD image processing algorithms or other processes are used to compare acquired images with images in the database. Such comparisons may provide feature vectors. Alternatively, such comparisons are used for CAD analysis or diagnostic determination.

Using various identified feature vectors or image information, one or more classifiers are invoked to provide a diagnosis. For example, the classifiers based on statistical models, a decision or rule based model, an artificial intelligence model and/or a neural network model are provided. Classifiers attempt proactive prediction or early stage disease detection based on historical data. For example, a neural network is programmed based on historical data indicating both abnormal and normal tissue. The underlying disease model information is used to predict a diagnostic decision. The diagnostic decision is based on the statistical information so that a predicted probability (e.g., degree of similarity) of the accuracy of the diagnosis is calculated. While an embodiment described for the above mentioned patent is based on a statistical classification, any of various now known or later developed classifiers may be used.

Since classifiers or the CAD database may be based in part on previously acquired data, current examination information, such as images or context data, may be used to update the database. As a result, future analyses performed based on the database may include information from currently acquired medical sensor data. As a result, a current user may model disease or shape the modeling of disease. For example, once a definitive diagnosis is provided through surgical examination, the database is updated with the previously acquired information. The training models are altered or updated to include any feature vector information from the current examination that may dictate or change the probability of normal versus abnormal diagnosis. By updating, the sensitivity of a particular diagnosis to one or more feature vectors is altered. The alteration occurs due to a direct change, processor based training or other algorithm. One or more displays or user interfaces may be provided for altering or updating the training models. In other embodiments, the ability of a user to update training models is limited or not allowed.

The CAD subsystem outputs diagnostic information based on the invoked classifiers in act 38. Any of numeral, graphical, textual or other evaluation information is presented to a user. For example, the results are displayed at a facility remote from the medical system, at the system, transmitted to a portable medical system or at a plurality of locations. Acts 40, 42 and 44 represent different alternative or cumulative outputs. FIG. 4 shows an example display of all three outputs.

In act 40, diagnostic results are output. For example, see application Ser. No. 60/454,112. One or more diagnoses with a probability exceeding a threshold amount are provided. Alternatively, all possible diagnoses are provided. In yet another alternative embodiment, the most probable or a certain number of most probable diagnoses are provided. For example, a list of likely diseases is output. Cases, images, measurements or other information similar or most similar to the currently analyzed case or possible diseases may optionally be provided. For example, a case most similar to the current examination associated with each of the diagnoses is provided. In one embodiment, a group of similar images to the current scan are displayed. Selection of a particular image results in display of a degree of similarity (e.g, percentage) with the current examination, anatomical position, technical tips, pitfalls, corresponding parameters (e.g., feature vectors or measurements), different views, views with different modes, sensitivities or other information. A most similar image is identified in one embodiment. A similarity rating is provided for one or more of the images. By selecting the similarity, available similar cases and their associated information are highlighted or made available to the user. While described above as output after CAD analysis, the similarity information or display may be included as part of the static menu structure that uses sonic CAD analysis or other algorithm to determine the degree of similarity during menu selection. As a result, a most similar case for each disease category is accessible to the user.

In one embodiment, the possible diagnoses are ranked. For example, the diagnoses are ranked in order of most probable to least probable. As yet another example, a numerical probability is associated or displayed with each of the possible diagnoses. In one embodiment, the user is allowed to restrict the number of possible diagnoses, such as restricting a list to the two most likely diagnoses. The restriction is provided prior to the output or as part of an interactive process after outputting a listing of possible diagnoses. The probability information is provided by the CAD analysis. The relational information or similarity determined by the classifier or classifiers used for a CAD analysis provides probability information for the current examination. Additional information may be provided, such as pitfalls, definitions, technical tips or other information related to each of the probable diseases.

FIG. 4 shows one possible output screen after CAD analysis. As represented at 50, a list of likely diagnoses is provided. Information associated with the highest probability is displayed. By selecting a lower probability diagnosis, the displayed information may change to show a closest case for the selected diagnosis in the other display boxes. The image acquired for the current examination is also displayed at 52 as well as an image from a most or other similar case at 54. A list of feature vectors, measurements or other related information is displayed at 56. The related information includes sensitivities, values associated with the current examination, values associated with the closest case and normal values. By selecting the recommendation tab or button at 58, any recommendations and associated information is provided. Alternatively, recommendations are provided within the box at 56, in a list on the display or in another manner. Any now known or later developed user interfaces may be used.

In act 42, a further act for diagnosis is recommended based on the CAD analysis. The further act is recommended automatically by the same or different processor used to perform the CAD analysis. For example, a processor and a medical sensor are used to jointly implement the CAD analysis and the automatic recommendation. Recommended further acts may include a recommended imaging view, acquisition of a different image, a medical protocol for further patient context information or medical sensor data, a measurement or other action by the user. In one embodiment, a plurality of further acts is recommended, such as a plurality of measurements, protocols, views and/or other acts. For example in breast imaging, sensitivity may be increased by fusing B-mode, acoustic streaming, strain, boost or other combination of information. Originally, a B mode is acquired. Depending upon analysis, output sensitivity may be increased with more measurements, analysis methods or acquisition methods. For example, further modes of acquisition are recommended, such as strain, stress-echo, contrast, and/or further measurements are recommended, such as a right heart assessment. A graphic representation of anatomy and/or probe position to scan particular anatomy may be provided with the recommendations, such as to assist in acquiring a desired full view of a possible disease.

The recommended further acts are identified by the CAD analysis. Missing information associated with a high, moderate or some probability of a disease state is identified. For example, a CAD database includes about 2000 echocardiograph multi-frame images, labeled by medical experts into different types and stages of cardiomyopathies. The database is used to determine that a left ventricle end diastolic dimension measured at 7.6 cm indicate a probability of a DCM at 86.2 percent. A 95 percentile indication of non DCM is provided by a measurement of less than 5.8 cm. The missing feature vectors are output to the user to provide a checklist of information associated with the current examination that may increase or decrease the diagnosis probability. Recommendations may additionally include performance of previously performed acts for increased accuracy associated with a feature vector. The recommendations prompt the user to acquire additional information to refine the diagnosis. The CAD database includes various features vectors associated with various diseases. Missing feature vectors are identified. In one embodiment, missing features vectors associated with a threshold amount or increased probability of abnormal or normal disease state are identified. In yet another embodiment, the recommendations are provided only for a diagnosis with a lesser than desired probability, such as a less than 90 percent probability of accuracy. Where a probable diagnosis is provided with no other equally or close diagnosis, further recommendations are not provided. Alternatively, recommendations are provided regardless of the probability of a given diagnosis or the relationship of one diagnosis to another diagnosis. The recommendations indicate a confusion matrix or list of information that may reduce ambiguity between different diagnoses or increase the probability of a particular diagnosis.

In one embodiment, the sensitivity of the diagnosis to a particular feature vector in the CAD analysis is used to identify further acts for recommendation. The available feature vectors for a particular examination are provided for analysis with classification models (e.g., likelihood maps). For example, see application Ser. No. 60/454,112. The output is a list of sensitive features providing additional measurements most likely to reduce uncertainty in classification. For example, a provided feature vector of a left ventricular end diastolic dimension of 7.6 indicates a high probability of a DOM. In a particular examination, the measurements for the left ventricle end systolic dimension, wall thickness (e.g., septum wall or posterior wall) and ejection fraction may not have been obtained. Since these additional measurements have a high probability of indicating DCM versus non DOM, these further measurements are recommended. A sonographer or doctor viewing the display can then determine, depending upon the known facts regarding a patient, whether these additional measurements should be taken.

In one embodiment, data responsive to performance of a further act is received. For example, one of the further acts recommended are performed, such as a further measurement. The CAD analysis of act 36 is then updated and the results determined and output to the user. By repeating the CAD analysis as a function of the medical sensor data, context data and data responsive to performance of the further act for the patient, a more accurate probability of a particular diagnosis is provided. The sonographer is able to achieve a more accurate medical diagnosis by performing the best or most likely significant measurements or other acts using the fewest number of acts. An iterative process may be performed where additional fewer acts are used to update the CAD analysis. Alternatively, multiple recommended further acts are performed prior to a repetition or repetitions of the CAD analysis of act 36. Based on the resulting probability of diagnoses, the sonographer may determine whether further recommended measurements are desired.

In act 44, the recommendations output in act 42 are associated with a sensitivity. The sensitivity indicates the likely effect on diagnosis of the missing recommended action. In one embodiment of indicating sensitivity, the recommended further acts are provided in rank or order of importance. For example, a left ventricle end systolic dimension, wall thickness, ejection fraction and other possible measurements are provided in the above order. The order then indicates that left ventricle end systolic dimension measurement is most important or most significant for confirming or indicating as a DCM versus non-DCM diagnosis. The sensitivity indication is calculated or obtained automatically by a processor, such as the same processor used for the CAD analysis and recommendation. Alternatively, a different processor is used. As an alternative to or in addition to ranking the plurality of further acts, a numerical value is output as the sensitivity for each or some of the further acts. For example, a confusion matrix indicating a predictability of a model or other information indicating where a diagnosis is lacking information is provided. Quantitative information assists the sonographer in determining whether to perform the further act. Where a high sensitivity is provided, the further act is likely to increase the accuracy or confirm a diagnosis. The sensitivity represents a statistical prediction of the disease occurrence and is provided through analysis of the CAD database information or feature vectors, such as the feature vectors provided in various training modules. By providing the sensitivity values, a sonographer is able to quantitatively and qualitatively assess a diagnosis. The feedback flow of FIG. 3 from the sensitivity or recommendation to either of configuring the medical system in act 30, obtaining scan data in act 32 or obtaining context data in act 34 represents the sonographer performing the further acts and repeating the CAD analysis of act 36.

FIG. 4 shows an output of a plurality of recommended further acts for one example CAD analysis. The further acts are in order of sensitivity, and sensitivity values are provided for a plurality of the further acts at 52. Through one or more feedbacks and performance of the CAD analysis of act 36, different outputs are provided. Once the further act is performed, a diagnosis is output in response to further act and the previously acquired medical sensor data. The diagnosis output is performed as a function of the measurement or other further act. Based on the updated information, the probability of the diagnosis is changed or updated. The information from the further act may increase a diagnosis probability, but may alternatively decrease or allow diagnosis probability to remain the same. Once the sonographer determines that the diagnosis is correct, the analysis is completed in act 46.

As an alternative or in addition to recommending further acts by the user, the further acts are automatically started or performed by the medical system or other processor. For example, a medical system is operable to obtain a measurement based on an image using an algorithm. The algorithm is implemented without further user input, but may include a request for further user input to assist in measurement. The resulting measurement or information from the further act is then automatically input for updating the CAD analysis. Automatic or interactive measurement tools that are now known or later developed may be invoked. For example, ejection fraction, wall motion or wall thickness measurements are provided. Wall motion measurements may include a request for a user to segment a wall and input subjective information associated with one or more segments. Alternatively, an automated process performs the segmentation and measures information associated with each segment. As further examples, contrast, strain or other enhanced features are available on and automatically performed by the medical sensor or processor. The additional information is then used to recalculate the probability of a particular diagnosis or diagnoses.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:
1. A method for assisting a medical diagnosis of a patient with a computer assisted diagnosis system, the method comprising:
 (a) configuring a medical system for a particular examination;
 (b) obtaining medical sensor data in response to the configuration of (a);
 (c) obtaining context data based on the configuration;
 (d) analyzing the medical sensor data and the context data as feature vectors with a processor;
 (e) automatically recommending a further act for diagnosis based on the analysis.

2. The method of claim 1 further comprising:
 (f) automatically reconfiguring the medical imaging system in response to the recommendation of (e).

3. The method of claim 2 wherein the reconfiguration of (f) comprises automatically performing the recommendation.

4. The method of claim 1 wherein (a) comprises connecting a transducer to the medical imaging system, the medical imaging system being an ultrasound system, the transducer being associated with at least the particular examination and not associated with another particular examination.

5. The method of claim 1 wherein (d) and (e) are preformed by the processor, the processor being in tbe medical imaging system.

6. The method of claim 1 wherein (a) comprises selecting the particular examination from an examination list.

7. The method of claim 1 wherein (a) comprises configuring the medical imaging system to obtain data and (c) comprises identifying the particular examination free of the data obtained as a result of a scan responsive to the configuration of (a).

8. The method of claim 1 wherein (d) comprises performing a computer assisted diagnosis.

9. The method of claim 1 wherein (e) comprises recommending a measurement.

10. The method of claim 1 wherein (e) comprises recommending imaging in a new mode.

11. The method of claim 10 wherein the new mode is one of: B-mode, C-mode, spectral Doppler, Doppler tissue imaging, strain imaging, elasticity imaging, shear wave imaging, acoustic streaming, acoustic palpation, harmonic imaging, boost imaging, 3-D, and 4-D.

12. The method of claim 1 wherein (e) comprises recommending an imaging view.

13. The method of claim 1 wherein (e) comprises recommending a medical protocol.

14. The method of claim 1 further comprising:
 (f) indicating a sensitivity of the recommendation of (e) for diagnosis.

15. The method of claim 14 wherein (e) comprises recommending a plurality of measurements where the further act is one of the plurality of measurements;
 wherein (f) comprises indicating a ranking of the plurality of measurements to a user.

16. The method of claim 14 further comprising:
 (g) outputting a probability of a diagnosis in response to (d), the sensitivity being based on an importance of the recommendation to the diagnosis.

17. The method of claim 1 further comprising;
(f) receiving data responsive to performance of the further act;
(g) repeating (d) as a function of the medical sensor data, the context data and the data responsive to performance of the further act for the patient; and
(h) outputting a probability of a diagnosis in response to (g).

18. The method of claim 1 further comprising:
(f) obtaining patient context data;
wherein (d) comprises analyzing the medical sensor data, the context data based on the configuration and the patient context data.

19. The method of claim 1 wherein (d) comprises analyzing based in part on a database; further comprising:
(f) updating the data base with the medical sensor data.

20. The method of claim 1 further comprising:
(f) identifying a measurement based on (d); and
(g) automatically performing the measurement;
wherein (e) is performed as a function of the measurement of (g).

21. A method for assisting a medical imaging diagnosis of a patient with a computer assisted diagnosis system, the method comprising:
(a) obtaining medical sensor data with a medical system;
(b) analyzing the medical sensor data with the computer assisted diagnosis system;
(c) identifying a further act to assist diagnosis based on the analysis;
(d) automatically performing the further act with the medical imaging system;
(e) outputting a diagnosis based on the further act and the medical sensor data;
(f) indicating a sensitivity of the further act of(c) for a first diagnosis; and
(g) indicating a probability of the first diagnosis
wherein (e) comprises outputting a probability of a second diagnosis updated from the first diagnosis with the information of the further act.

* * * * *